United States Patent
Weise

(10) Patent No.: US 6,902,029 B2
(45) Date of Patent: Jun. 7, 2005

(54) RETRACTABLE EAR PROTECTION DEVICE

(75) Inventor: Jon Weise, Roselle, NJ (US)

(73) Assignee: Owl Investors of Texas, LLC, Marshall, TX (US)

( * ) Notice: Subject to any disclaimer, the term of this patent is extended or adjusted under 35 U.S.C. 154(b) by 9 days.

(21) Appl. No.: 10/020,744

(22) Filed: Oct. 30, 2001

(65) Prior Publication Data

US 2003/0079935 A1 May 1, 2003

(51) Int. Cl.⁷ .................. H04R 25/02; B65H 75/42; A61F 11/08
(52) U.S. Cl. ............ 181/129; 181/130; 242/388.6; 128/867
(58) Field of Search .................. 181/129, 130, 181/135; 2/423, 209; D29/112; D14/249; D24/106, 174, 173; 128/864, 867; 242/169, 388.6, 389, 396.4, 404.2, 404.3

(56) References Cited

U.S. PATENT DOCUMENTS

| | | | |
|---|---|---|---|
| 3,970,082 A | * 7/1976 | Leight | 128/866 |
| D277,317 S | * 1/1985 | Eisenmenger | D24/106 |
| 4,802,638 A | * 2/1989 | Burger et al. | 242/388.1 |
| 4,867,149 A | * 9/1989 | Falco | 128/864 |
| 5,231,704 A | * 8/1993 | Hildenbrand | 2/423 |
| 5,279,473 A | * 1/1994 | Rozon | 242/377 |
| 5,332,171 A | * 7/1994 | Steff | 242/378 |
| 5,332,871 A | * 7/1994 | Carrigan | 181/135 |
| 5,339,461 A | * 8/1994 | Luplow | 455/351 |
| 5,581,821 A | * 12/1996 | Nakano | 2/422 |
| 5,630,456 A | * 5/1997 | Hugo et al. | 160/173 R |
| 5,684,883 A | * 11/1997 | Chen | 381/385 |
| 5,853,136 A | * 12/1998 | Lai | 242/388.1 |
| 5,957,136 A | * 9/1999 | Magidson et al. | 128/864 |
| 5,984,224 A | * 11/1999 | Yang | 242/400.1 |
| 5,988,313 A | * 11/1999 | Håkansson | 181/135 |
| 6,006,857 A | * 12/1999 | Leight et al. | 181/135 |
| 6,082,855 A | * 7/2000 | Fleming | 351/123 |
| 6,340,227 B1 | * 1/2002 | Solberg et al. | 351/123 |
| 6,416,005 B1 | * 7/2002 | Liao | 242/378.1 |
| 6,474,585 B2 | * 11/2002 | Liao | 242/378.1 |
| 6,497,378 B1 | * 12/2002 | Liao | 242/378.1 |
| 2002/0023814 A1 | * 2/2002 | Poutiatine | 191/12.2 R |
| 2002/0137554 A1 | * 9/2002 | Hanna et al. | 455/568 |
| 2003/0019015 A1 | * 1/2003 | Hugh et al. | 2/265 |

FOREIGN PATENT DOCUMENTS

| | | | | |
|---|---|---|---|---|
| JP | 08237349 A | * 9/1996 | | H04M/1/15 |
| JP | 10297836 A | * 11/1998 | | B65H/75/48 |

* cited by examiner

Primary Examiner—Edgardo San Martin
(74) Attorney, Agent, or Firm—Ward & Olivo

(57) ABSTRACT

The invention disclosed provides an improved ear protection system comprising an ear protection device and an innovative stowage device. The stowage device is capable for inconspicuously securing the ear protection device to an easily accessible entity such as an article of clothing. The system is further able to accommodate various sizes and shapes of ear protection devices at varying distances and lengths from the user's ear. Additionally incorporated in the ear protection system is a locking mechanism to control the extension and retraction of the ear protection device from th stowage device.

36 Claims, 3 Drawing Sheets

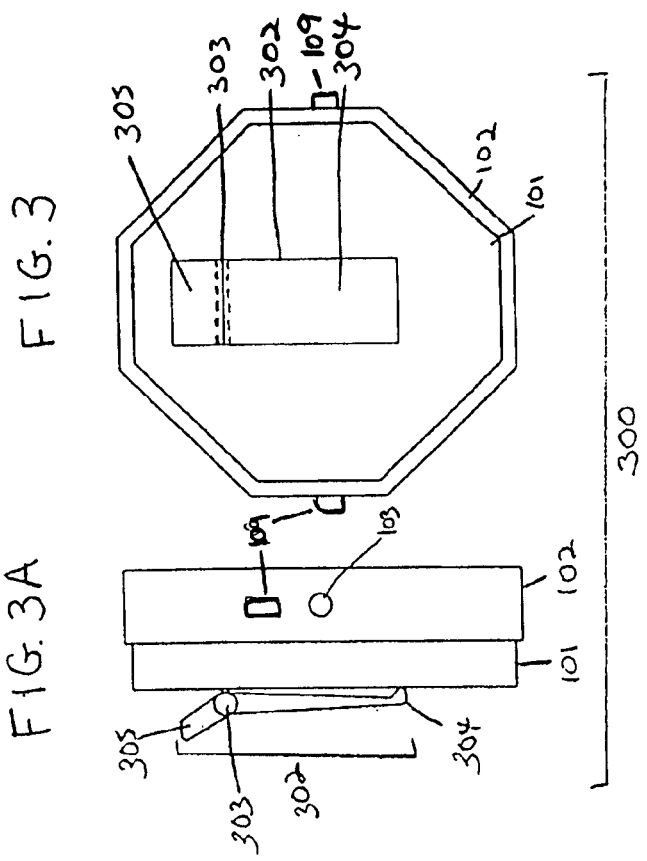
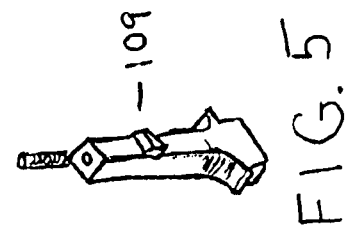
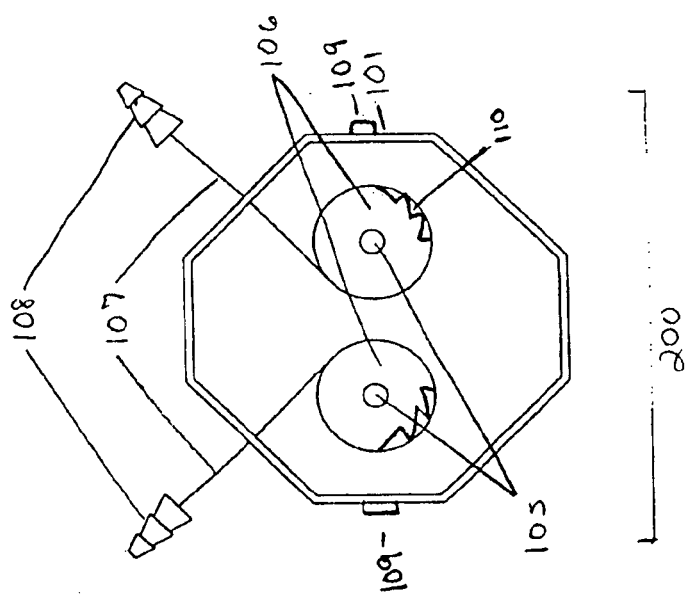
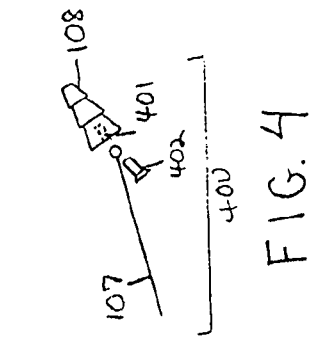

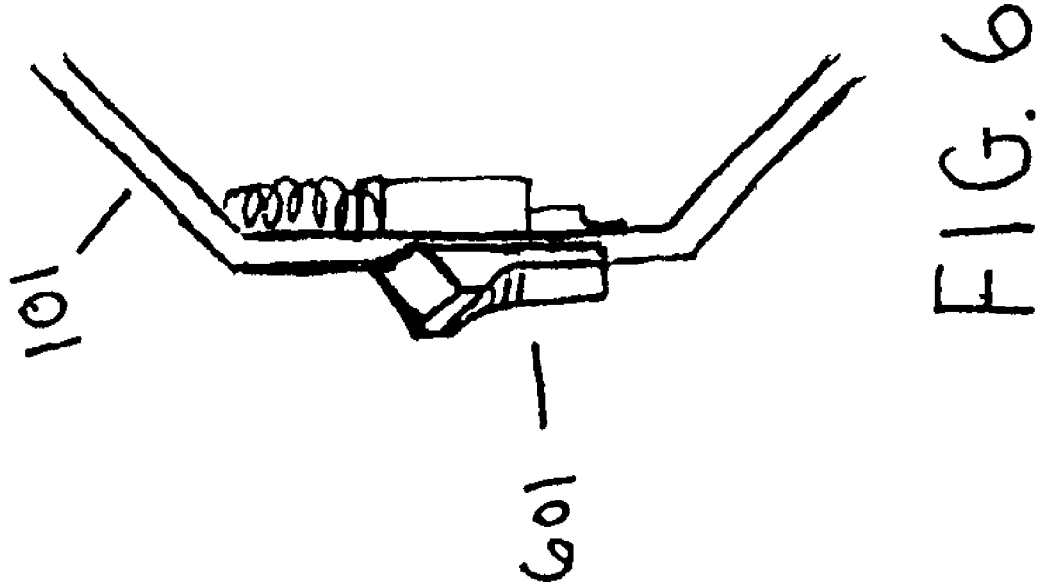

RETRACTABLE EAR PROTECTION DEVICE

FIELD OF THE INVENTION

This invention relates to the field of ear protection systems, and in particular, means for stowage of protective ear devices. Further, the invention relates to an encasement for ear protection devices with means for extension and retraction of protective ear devices.

BACKGROUND OF THE INVENTION

Prolonged exposure to environments with insalubrious sounds may be detrimental to hearing and may even cause deafness. Earplugs and ear protection devices have been developed to prevent harm to the eardrum and allow individuals to endure extended time in such environments without harm.

One of the first types of well-known protective earplugs in the United States was the "V-51 R". This earplug was developed during World War II in order to provide improved hearing protection to members of the military who were subjected to the concussive sounds of gunfire, explosions, and extremely noisy work environments, such as at airports or aircraft maintenance facilities.

Today earplugs are more commonly used in manufacturing and research environments where workers' ears must be protected against very loud, acoustically "high" or treble sounds. These sounds are painful to the ear and can permanently damage a person's sense of hearing.

There have been three common ear protection devices developed to seal the ears of people against loud and harmful sounds, which may occur in environments such as a factories, laboratories, airports and during use of certain machinery. One type is a self-sufficient ear protection device with most of the device entering the ear canal, and which holds itself in position by friction between the earplug and the ear canal of the wearer. The second type of ear protection device has no involvement with the ear canal and is characterized by the requirement of an apparatus, such as a headband, to secure the device in place. The device may either fully cover the ear or seal against the inside walls of the ear. The third device comprises a combination of a form of self-sufficient earplugs coupled to an apparatus.

Self-sufficient earplugs are usually constructed of soft resilient material, cylindrical or slightly tapered and larger than the acoustical canal of the ear. By wedging the plugs into the ear canal, the exterior surface of the plugs conforms to the ear canal and the central portion of the plug inhibits the penetration of loud and harmful sounds to the ear canal. Such earplugs can be constructed by injection molding a foamable material into a die, which forms a foam body with a smooth thin skin on the outside.

The second type of device comprises ear protection devices mounted at opposing ends of a band that extends halfway about the wearer's head. Traditionally, each earplug seals against the walls of the ear, which surround the entrance to the ear canal. Although not as effective in preventing sound, the ear protection device attached to a band may consist of a full ear covering. Many people also object to inserting objects into their ear canal, as with self-sufficient ear protection devices. This device eliminates that concern. However, unlike the ear canal, which is largely cylindrical and more easily sealed against, the walls surrounding the entrance to the ear canal are of a more irregular shape. Therefore, it is much more difficult to construct a form fitting apparatus to effectively prevent the sounds from penetrating into the ear canal.

One disadvantage of self-sufficient ear protection devices are the difficulty an individual encounters when attempting to remove them. When workers handle the earplugs by grasping them, they sometimes pinch the outer skin, which causes it to crack and become irritated. Moreover, when such an earplug body is pressed into the ear canal, the skin on the plug body does not uniformly contract, so wrinkles may be created through which sound can pass to reduce the effectiveness of the earplug.

A drawback with both types of protective ear devices is the proper placement and stowage of the earplugs when not in use. When the noise level is not high, workers often wish to remove the ear protection device from their ears to allow for better hearing of sounds and avoiding the discomfort of earplugs. Self-sufficient earplugs, however, are usually small and easily misplaced. Band earplugs are cumbersome and arduous to store and carry.

A combination of the self-sufficient and band types of ear protection was introduced to address the issue of where to place the ear protection device when not in use. This type of hybrid ear protection device was designed as self-sufficient, but coupled to an apparatus, such as a helmet or protective glasses. The ear protection devices are usually coupled to the apparatus through cords or bar attachments. The length of these attachments typically is preset and only minor alternations are possible.

This third approach does not, however, provide a secure place to stow the device when it is not in use. Additionally, it is limited because users may find that a helmet or protective glasses are not always necessary. For example, if an individual works in proximity to a loud factory area or in an airport, eye and head protection are not required, but ear protection would still be advantageous.

An additional disadvantage of the aforementioned ear protection devices is that they are unattractive. If the user perceives the appearance to be unattractive, he or she may choose to refrain from using the protector, leading to unnecessarily increased danger. It would be desirable to design such an apparatus that is inconspicuous or visually pleasing.

SURVEY OF PRIOR ART

In order to provide background information so that the invention may be completely understood and appreciated in its proper context, reference may be made to a number of patents and products:

The "V-51 R" is one example of a self-sufficient type of earplug. The "V-51 R" earplug is composed of a resilient elastomeric material, neoprene rubber, and comprises a single retroverted flange element extending from the nose end of a tubular rubber stalk member. The flange element extends rearwardly from the nose of the tubular rubber stalk. During use, the earplug is forcibly inserted into the ear canal, thereby at least partially collapsing the rearward extending flange element into the underlying free annular space and conforming said flange element into an acoustic sealing relationship with the constraining walls of the ear canal.

Leight U.S. Pat. No. 3,970,082 teaches of an ear protector assembly mounted to a protective helmet. Leight exemplifies the desire to incorporate a means for stowage in ear protection devices. Leight discloses an ear protection assembly coupled through a linkage to the helmet consisting of pivotal bars allowing for alignment with the ear canal of the wearer. The linkage may move around the rim of the helmet and rest upon the rim for stowage. Although the invention provides a means for stowage, it is a complex, bulky contraption that lacks a visually pleasing façade. Additionally, the requirement of wearing a helmet can be unnecessary and uncomfortable.

A self-sufficient ear protection device is described in Falco U.S. Pat. No. 4,867,149, disclosing a solid shaft member to support multiple flanges. The central solid shaft member has the advantage of allowing the earplug to be fully inserted into the ear canal as long as the material is of a sufficient hardness to allow for this full insertion. This type of earplug can create discomfort in the wearer because these self-sufficient earplugs exert excessive pressure on the walls of the ear canal. This earplug disclosed in Falco is also subject to easy misplacement.

Hildenbrand U.S. Pat. No. 5,231,704 depicts an ear protection device attachable to chin straps of a helmet. The ear device comprises a covering member, which is positioned on or around the chinstraps and in contact with the bottom edge of the helmet. This device provides an attachment means, yet no means for stowage. This device also requires the inconvenient, unattractive and possibly unnecessary action of wearing a helmet.

Carrigan U.S. Pat. No. 5,332,871 discloses an improved efficiency earplug entitled "Sliding Valve Earplug". It includes an earplug body having successive and larger rubber hemispheres mounting a valve body to the ear. The valve body defines an aperture centrally of the plug body and central to the ear canal. A slide acts as an acoustical valve seat and selectively opens and closes the valve body. This slide is linear in motion; its size and excursion is dependent upon the physiology of the ear. It brings a sound-transmitting aperture in the slide into and out of registry to permit sounds to directly reach the ear. While this invention improved the efficiency of earplugs it did not teach anything related to the stowage or encasement of earplugs. As with the aforementioned self-sufficient earplug designs, the problems of discomfort and easy misplacement still persist.

Magidson, et al. U.S. Pat. No. 5,957,136 teaches of an earplug composed of a polymeric material and the method for manufacturing said earplugs. This design includes a hollow member with an open end and a closed end having a rounded cone shape configuration. There is an additional member extending from the first member with the similar configuration but with a larger diameter. The novel shape of the invention improves the earplug in terms of efficiency, yet it does not address the problems of stowage and encasement. Therefore, Magidson teaches nothing that helps to remedy the discomfort and easy misplacement which are eliminated by the present invention.

H.ang.kansson U.S. Pat. No. 5,988,313 depicts an earplug made of an elastic polymeric material and the method for manufacturing it. The earplug comprises an elongated core and a sealing part connected with the core. The sealing part consists of a softer material. This invention provides a desirable improvement in conformability of earplugs with the ear, but does not mention stowage or encasement means. The design strives to eliminate the discomfort of earplugs, yet only reduces it. It would be desirable to provide an easily accessible means of stowage, such as in the present invention, to further diminish the discomfort of earplugs. Whenever an individual experiences discomfort the earplugs may be removed and temporarily stowed until the discomfort has ceased. Further, H.ang.kansson does not address the issue of easy misplacement.

Fleming U.S. Pat. No. 6,082,855 describes an earplug mounted on an eyeglass temple bar that can fit into the ear canal. The coupling includes a wire of resilient plastic that is wound into a tight helix. This invention was designed to curtail movement of the earplugs, yet does not eliminate it. The earplugs are located on a tight helix cord and hang freely from the eyeglasses. Thus, in environments requiring extensive movement, the earplugs become a nuisance. Further, the plugs cannot be used without the glasses, and requiring eyeglasses is often inconvenient, unattractive and unnecessary.

Leight, et al. U.S. Pat. No. 6,006,857 discloses an earplug with an increased ability to block noise. The earplug comprises a soft shell and an insertion stem facilitating the removal of the earplug. This invention does not address the need to inconspicuously stow the earplugs when not in use.

Whatever the merits, features and advantages of the above-cited references, none provide a comfortable, easily storable and aesthetically pleasing ear protection device. For example, providing an effective earplug with convenient, accessible stowage means presents a unique problem, which is not satisfactorily addressed by any of the prior art. Attempts to achieve this objective by the above and other related prior art have resulted in complex contraptions which are awkward in nature or require additional undesirable and often unnecessary elements, such as a helmet or protective glasses.

What is needed is a more adaptable stowage means for ear protection devices, which can be easily accessible, inconspicuously placed, free of complexity and bulk and focused on ear protection specific to an individual.

SUMMARY OF THE INVENTION

The present invention comprises an apparatus for both ear protection and stowage means. The apparatus embodies a means for coupling an ear protection device, such as an earplug, with the stowage device including a means for extension and retraction. The apparatus further includes a means for attaching the stowage device to any variety of easily accessible entities, such as the front or back collar of a shirt.

The encasement of the apparatus in the present invention comprises an anterior and a posterior member, which are secured together. The members are attached in a means that may be separated when desirable, such as with screws. Thus, an individual may conveniently alter any interior part of the device. Additionally, the members may be constructed of durable, sturdy plastic for prolonged usage.

Mounted on the exterior of the encasement is a rotatable means for coupling the device to an entity for storage of the encasement. The means can include a clip which may rotate 360 degrees along an axis perpendicular to the encasement. The clip may secure the encasement to an easily accessible object. For example, a clip may be mounted to the exterior of the encasement for attaching the device inconspicuously to the back collar of a shirt. Thus, the ability to attach the encasement to a variety locations make it easily accessible, lessens the possibility of misplacement and eliminates the unnatural and awkward appearance of the traditional ear protection stowage devices, such as helmets eyeglasses.

The means for coupling each ear protection device to the encasement for the present invention may comprise an extendable and retractable cord. The method of extension and retraction may embody a spool for each cord mounted on a corresponding protruding axis. The axes are secured to the interior of the posterior member of the encasement. A spool rotates in one direction to extend the cord and the reverse to retract the cord.

The spools may incorporate additional features such as a spring-loaded locking mechanism for controlling the extension and retraction of the cord. The locking mechanism may include any of a variety of components, such as a ratchet, pushbutton or thumb slide. Upon extension to a desired length, a locking mechanism may prevent further movement of the spool. Upon release of the locking mechanism, when usage of the earplugs is no longer desired, the spool will rotate in the reverse direction to retract the cord with the corresponding ear protection device to the encasement. For example, the locking mechanism may incorporate a spring-loaded spool favoring the fully retracted position. The cord may be pulled to the desired extended length. A pushbutton may then be pressed to lock the position of the spool and prevent further movement in either direction.

Upon release of the pushbutton, the cord will retract to the encasement providing secure placement of the ear protection device when not in use. A thumb slide functions in a similar manner. To prevent motion of the spool the thumb slide can be moved to one side of a thin slot. Once moved to the opposing side the spool would be released. The length of the cord can vary and may extend to as much as one and a half feet or more.

Furthermore, the present invention may comprise interchangeable self-sufficient ear protection means coupled to the retractable cord. Therefore ear protection means may be changed whenever necessary or desired. For example, it may be desirable to alter or change the earplugs when they have become deformed or when a different individual requests to use the device. Additionally, the device may be used in conjunction with ear protection means in a variety of sizes or types, thus an individual may select their optimum ear protection means. The interchangeable ear protection means may be secured through the use of screws or similar means.

It is an objective of the present invention to provide a durable device for stowage of ear protection means.

It is another objective of the present invention to include means for coupling the ear protection device with the encasement.

It is a further objective of the present invention for extendable and retractable coupling means.

An additional objective of the present invention is to include a means for attachment of the encasement to an accessible entity.

Still a further objective of the present invention is for the encasement to include a visually pleasing façade.

Another objective of the present invention is to allow interchangeability of various ear protection devices.

BRIEF DESCRIPTION OF FIGURES

A further understanding of the present invention can be obtained by reference to a preferred embodiment as set forth in the illustrations of the accompanying drawings. Although the illustrated embodiment is merely exemplary of systems for carrying out the present invention, both the organization and method of operation of the invention, in general, together with further objectives and advantages thereof, may be more easily understood by reference to the drawings and the following description. The drawings are not intended to limit the scope of this invention, but merely to clarify and exemplify the invention.

FIG. 2 depicts a front perspective portrayal of the interior of the encasement of the preferred embodiment of the present invention.

FIG. 3 depicts a perspective portrayal of the back view of the preferred embodiment of the present invention.

FIG. 3A depicts a perspective portrayal of the side view of the preferred embodiment of the present invention.

FIG. 4 depicts an exploded view of the means for coupling an interchangeable ear protection device to the retractable cord of the preferred embodiment of the present invention.

FIG. 5 depicts a detailed view of the pushbutton of the preferred embodiment of the present invention.

FIG. 6 depicts an alternative embodiment of the present invention incorporating a thumbslide instead of a pushbutton.

DETAILED DESCRIPTION OF THE PREFERRED EMBODIMENTS

Figure 1:
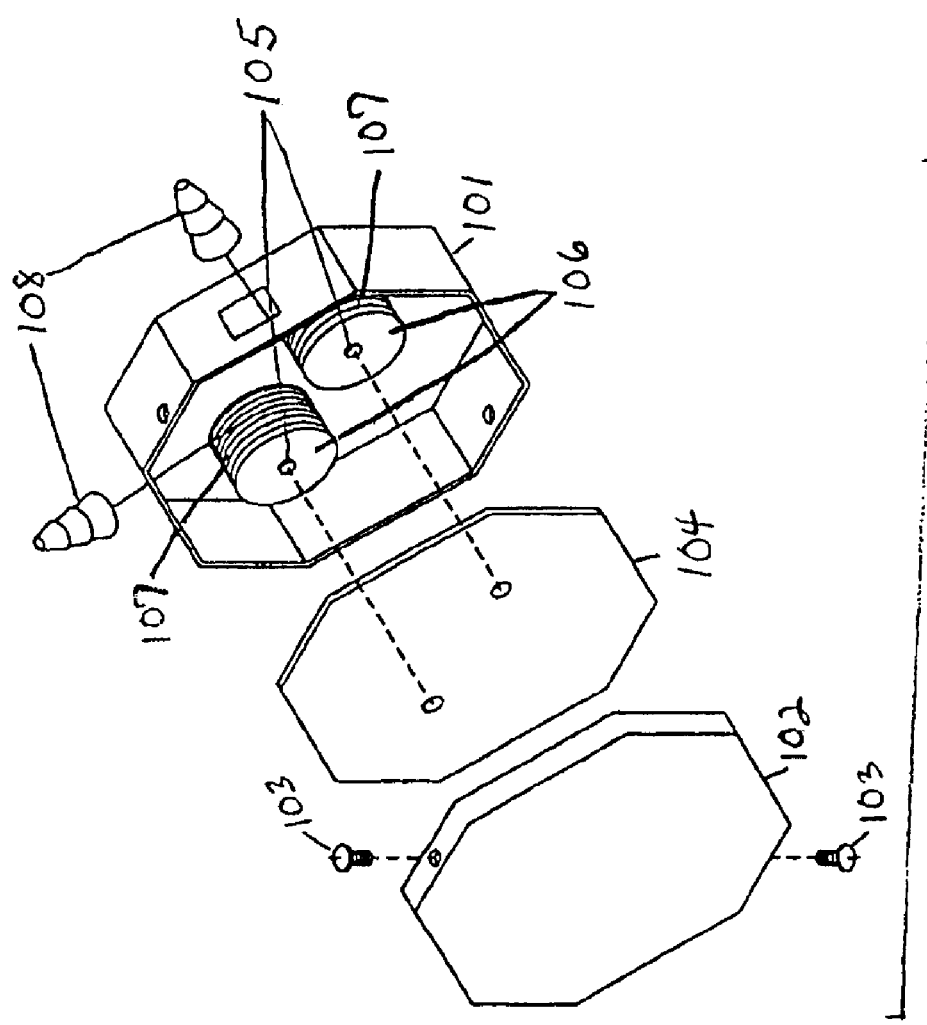
FIG. 1 depicts an assembly portrayal of the preferred embodiment of the present invention.

As required, a detailed illustrative embodiment of the present invention is disclosed herein. However, techniques, systems and operating structures in accordance with the present invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure. The following presents a detailed description of several preferred embodiment of the present invention.

FIG. 1 depicts an assembly portrayal 100 of components of the preferred embodiment of the present invention. The assembly 100 comprises a two-member encasement, anterior 101 and posterior 102 with a medial member 104. The anterior 101 and posterior 102 members can be constructed of a durable plastic. The posterior member 102 is a cover for the encasement, which could contain a logo, decal or other ornamentation to enhance the appearance of the device on the exterior. The anterior member 101 is fixed to the posterior member 102 with screws 103. The encasement may conveniently be uncovered by removing the screws 103. The medial member 104 is securely placed just within the posterior member 102 encasement edges to prevent the movement of the entities within the encasement.

Within the encasement, two axes 105 protrude from the interior of the anterior member 101. Each axis supports a spool 106, wound with a non-elastic cord 107. Each spool 106 rotates in one direction to extend the cord 107 and rotates in the reverse direction to retract the cord 107. Each axis 105 will incorporate a spring-loaded locking mechanism (not shown) to control the extension and retraction of the cord 107. The locking mechanism incorporates a ratchet device that favors the extension direction of the cord 107. The cord 107 may then be freely extended to the desired length. The cord 107 will then remain at the desired length until the unlocking of the ratchet device, possibly by slightly pulling the cord 107 in a certain direction. The cord 107 will then be free to retract to the encasement providing secure placement for an ear protection device.

The opposing end of each non-elastic cord 107 is coupled to ear protection devices 108. The ear protection devices 108 may comprise efficient self-sufficient earplugs constructed of a resilient material. With the attachment to the cord 107, the earplugs 108 may be freely extended and retracted. Additionally, the earplugs 108 may be easily removed from an individual's ear by simply pulling on the cord 107, eliminating the cracking of the skin that results from the use of other self-sufficient earplugs. Upon full retraction of the cord 107 the earplugs 108 are securely stowed against the encasement.

FIG. 2 depicts a front perspective portrayal of an embodiment of the present invention without the covering of the anterior member 200. Within the posterior member 101, the two axes 105 are located horizontally adjacent to each other and at the vertical center of the encasement 200. A spool 106 is mounted to each axis 105 wound with a non-elastic cord 107. A ratchet 110 prevents the spools from rotating in the reverse direction. Additionally shown is pushbutton 109 which operates to lock the position of the spool. Each spool may have its own pushbutton as illustrated. A more detailed view of pushbutton 109 is shown in FIG. 5.

FIG. 3 depicts a back perspective portrayal and FIG. 3A depicts a side perspective of the preferred embodiment of the present invention 300. The invention 300 incorporates a means for coupling the encasement to an easily accessible entity. The means for coupling is mounted to the exterior of the anterior member 101 of the encasement. The means for coupling comprises a clip 302 possibly constructed of the same material as the encasement members. The clip 302 incorporates a helical spring 303 providing means for the lower section 304 of the clip 302 to withdraw from the encasement when pressure is applied to the upper portion 305 of the clip 302. The clip 302, while open, may be placed adjacent to the desired entity to be attached. When the pressure is released on the upper section 305 then the lower section 304 closes securing the encasement to the desired entity. The clip may rotate 360 degrees along an axis perpendicular to the encasement. Additionally, visibly in the side perspective portrayal, the screw 103 secures the anterior 101 and posterior 102 members together.

FIG. 4 depicts an exploded isometric view of the coupling of an ear protection device 108 and end of the non-elastic cord 107. The present invention was designed to include interchangeability of the ear protection device 108. The interior of the ear protection device 108 comprises a threaded cavity 401. Any size or type of ear protection device with a threaded cavity 401 of the corresponding diameter of the screw 402 may be coupled onto the cord. Thus, an individual may select the protective ear device that provides maximum efficiency and minimal discomfort.

FIG. 6 depicts an alternative embodiment of the present invention incorporating thumbslide 601 in place of a pushbutton. Thumbslide 601 operates in a similar manner to pushbutton 109, preventing motion of the spool when moved to one side. The spool is released when thumbslide 601 is moved to the opposing side.

While the present invention has been described with reference to one or more preferred embodiments, which embodiments have been set forth in considerable detail for the purposes of making a complete disclosure of the invention, such embodiments are merely exemplary and are not intended to be limiting or represent an exhaustive enumeration of all aspects of the invention. Further, it will be apparent to those of skill in the art that numerous changes may be made in such details without departing from the spirit and the principles of the invention.

I claim:

1. An ear protection system consisting of:
    a plurality of ear protection devices for preventing the penetration of harmful or disturbing sounds into the ear canal,
    an encasement structure comprising at least an anterior member and posterior member, wherein said anterior member and said posterior member are coupled together;
    a plurality of retraction means disposed within said encasement structure for selectively retracting said plurality of ear protection devices toward said encasement structure; and
    a mounting means for removably mounting said encasement structure upon an entity for convenient placement of said encasement structure;
    wherein said plurality of retraction means operates said plurality of ear protection devices independently; and
    wherein said ear protection devices are independent of one another.

2. An ear protection system according to claim 1, wherein said plurality of ear protection devices comprise earplugs.

3. An ear protection system according to claim 2, wherein said earplugs are removably coupled to said retraction means.

4. An ear protection system according to claim 1, wherein said plurality of ear protection devices are independently removable and coupled to said retraction means.

5. An ear protection system according to claim 1, wherein the interior of said encasement structure comprises protruding axes perpendicular to said anterior member.

6. An ear protection system according to claim 1, wherein said encasement structure is constructed of plastic.

7. An ear protection system according to claim 1, wherein said retraction means comprises a cord for coupling said plurality of ear protection devices to said encasement structure.

8. An ear protection system according to claim 7, wherein said retraction means comprises spools for mounting said cord.

9. An ear protection system according to claim 1, wherein said retraction means comprises a spring loaded locking mechanism for securing the extension of said plurality of ear protection devices.

10. An ear protection system according to claim 9, wherein said spring loaded locking mechanism comprises a thumb slide.

11. An ear protection system according to claim 9, wherein said spring loaded locking mechanism comprises a push button.

12. An ear protection system according to claim 9, wherein said spring-loaded locking mechanism comprises a ratchet.

13. An ear protection system according to claim 1, wherein said mounting means comprises a clip-on means.

14. An ear protection system according to claim 13, wherein said clip-on means is rotatable.

15. A method of ear protection consisting of the steps of:
    providing an encasement structure comprising at least an anterior member and posterior member, wherein said anterior member and said posterior member are removably coupled together;
    preventing the penetration of harmful or disturbing sounds into the ear canal by providing a plurality of ear protection devices;
    selectively retracting at least one of said plurality of ear protection devices, wherein said selectively retracting is executed by at least one of a plurality of independent retraction means;
    securely stowing said plurality of ear protection devices adjacent to said encasement structure; and
    mounting said encasement structure upon an entity for convenient placement of said encasement structure with removable mounting means.

16. A method of ear protection according to claim 15, wherein said ear protection devices are independently removable and coupled to said retraction means.

17. A method of ear protection according to claim 15, wherein the interior of said encasement structure comprises protruding axes, wherein said protruding axes are perpendicular to said anterior member.

18. A method of-ear protection according to claim 15, wherein said retraction means comprises a cord mounted on spools.

19. A method of ear protection according to claim 15, wherein said retraction means comprises a cord mounted on spools; and wherein said interior of said encasement structure comprises protruding axes, wherein said protruding axes are perpendicular to said posterior member; further wherein said spools are mounted on said protruding axes of said encasement structure.

20. A method of ear protection according to claim 15, wherein said retracting step comprises securing each of the extensions of said plurality of ear protection devices by a spring loaded locking mechanism.

21. A method of ear protection according to claim 20, wherein said spring-loaded locking mechanism comprises a thumb slide.

22. A method of ear protection according to claim 20; wherein said spring-loaded locking mechanism comprises a push button.

23. A method of ear protection according to claim 20, wherein said spring-loaded locking mechanism comprises a ratchet.

24. An ear protection system consisting of:
   a plurality of ear protection devices for preventing the penetration of harmful and disturbing sounds into the ear canal,
   an encasement structure comprising at least two members, wherein said members are coupled together; further, wherein said encasement structure is coupled to said ear protection device; and
   a mounting means for removably mounting said encasement structure upon an entity for convenient placement of said encasement structure;
   wherein said plurality of ear protection devices are coupled to said encasement means by a plurality of retraction means for selectively retracting said plurality of ear protection devices toward said encasement structure;
   wherein said plurality of retraction means operate said plurality of ear protection devices independently; and
   wherein said ear protection devices are independent of one another.

25. An ear protection system according to claim 24, wherein said ear protection devices comprise earplugs.

26. An ear protection system according to claim 24, wherein said plurality of ear protection devices are independently removable and coupled to said encasement structure.

27. An ear protection device according to claim 24, wherein said plurality of ear protection devices are independently removable and coupled to said plurality of retraction means.

28. An ear protection system according to claim 24, wherein each of said plurality of retraction means comprises a cord for independently coupling each of said plurality of ear protection devices to said encasement structure.

29. An ear protection system according to claim 28, wherein said retraction means comprises spools for mounting said cord.

30. An ear protection system according to claim 24, wherein said retraction means comprises a spring-loaded locking mechanism for securing the extension of said plurality of ear protection devices.

31. An ear protection system according to claim 30, wherein said spring-loaded locking mechanism comprises a thumb slide.

32. An ear protection system according to claim 30, wherein said spring-loaded locking mechanism comprises a push button.

33. An ear protection system according to claim 30, wherein said spring-loaded locking mechanism comprises a ratchet.

34. An ear protection system according to claim 24, wherein said encasement structure is constructed of plastic.

35. An ear protection system according to claim 24, wherein said mounting means comprises a clip-on means.

36. An ear protection system according to claim 35, wherein said clip-on means is rotatable.

* * * * *